United States Patent
Fuhr et al.

(10) Patent No.: US 9,464,973 B2
(45) Date of Patent: Oct. 11, 2016

(54) SAMPLE SUPPORT AND SAMPLE STORE, ESPECIALLY FOR THE CRYOPRESERVATION OF BIOLOGICAL SAMPLES

(75) Inventors: Günter R. Fuhr, Berlin (DE); Heiko Zimmermann, St. Ingbert (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 1546 days.

(21) Appl. No.: 12/162,136

(22) PCT Filed: Jan. 19, 2007

(86) PCT No.: PCT/EP2007/000465
§ 371 (c)(1),
(2), (4) Date: Jul. 25, 2008

(87) PCT Pub. No.: WO2007/085385
PCT Pub. Date: Aug. 2, 2007

(65) Prior Publication Data
US 2009/0029341 A1     Jan. 29, 2009

(30) Foreign Application Priority Data
Jan. 27, 2006   (DE) .................. 10 2006 003 995

(51) Int. Cl.
*A01N 1/02* (2006.01)
*G01N 1/42* (2006.01)
(Continued)

(52) U.S. Cl.
CPC   *G01N 1/42* (2013.01); *A01N 1/00* (2013.01); *A01N 1/02* (2013.01); *A01N 1/0268* (2013.01);
(Continued)

(58) Field of Classification Search
CPC .......... B65D 21/0233; B65D 21/0209; B65D 2577/045; A01N 1/0268; G01N 1/42
USPC ....................................... 435/307.1
See application file for complete search history.

(56) References Cited

U.S. PATENT DOCUMENTS 3,067,896 A * 12/1962 Berg ............... A47J 41/028
                                                            215/10
3,819,081 A *  6/1974 Runte .................. 220/23.87
(Continued)

FOREIGN PATENT DOCUMENTS

DE         3903645 A1      8/1989
DE        10203940 A1      8/2003
(Continued)

OTHER PUBLICATIONS

International Search Report for PCT/EP2007/000465.

*Primary Examiner* — Jonathan Hurst
(74) *Attorney, Agent, or Firm* — Caesar Rivise, PC (57) ABSTRACT

A sample support (100, 101, 102, . . . ), in particular for cryopreservation of biological samples, is described and includes: a holder part (10) with a sample receiving chamber (11), a retaining device (12, 13) on which a sample can be disposed, and support connecting elements (14, 15) which are directed at opposite holder part ends (16, 17) and are formed to fit together so that a plurality of holder parts (16) can be put together. A sample store (200), which includes an assemblage of a large number of such sample supports, and a method for the cryopreservation of biological samples, are also described.

30 Claims, 7 Drawing Sheets

(51) Int. Cl.
*A01N 1/00* (2006.01)
*B01L 3/00* (2006.01)

(52) U.S. Cl.
CPC ...... *B01L 3/50855* (2013.01); *B01L 2200/025* (2013.01); *B01L 2300/022* (2013.01); *B01L 2300/024* (2013.01); *B01L 2300/041* (2013.01); *B01L 2300/0832* (2013.01); *B01L 2300/0838* (2013.01); *B01L 2300/1894* (2013.01)

(56) References Cited

U.S. PATENT DOCUMENTS

| | | | |
|---|---|---|---|
| 5,197,602 A * | 3/1993 | Biesecker et al. | 206/514 |
| 5,346,083 A * | 9/1994 | Song | B65D 1/023 215/341 |
| 6,145,688 A * | 11/2000 | Smith | 220/259.3 |
| 6,197,573 B1 * | 3/2001 | Suryanarayan et al. | 435/286.7 |
| 6,446,807 B1 | 9/2002 | Lafond et al. | |
| 6,752,967 B2 | 6/2004 | Farina et al. | |
| 6,758,362 B2 | 7/2004 | Studer | |
| 7,410,055 B2 | 8/2008 | Plank | |
| 7,458,285 B2 | 12/2008 | Fuhr et al. | |
| 2002/0108957 A1 | 8/2002 | Studer | |
| 2003/0086830 A1 * | 5/2003 | Haywood et al. | 422/102 |
| 2003/0129095 A1 | 7/2003 | Farina et al. | |
| 2004/0171141 A1 | 9/2004 | Plank | |
| 2005/0196746 A1 * | 9/2005 | Xu et al. | 435/4 |
| 2006/0013728 A1 * | 1/2006 | Moir | 422/61 |
| 2006/0131196 A1 | 6/2006 | Fuhr et al. | |
| 2006/0154232 A1 | 7/2006 | Degel et al. | |
| 2006/0188865 A1 | 8/2006 | Fuhr et al. | |

FOREIGN PATENT DOCUMENTS

| | | |
|---|---|---|
| DE | 10251721 A1 | 5/2004 |
| DE | 10251722 A1 | 5/2004 |
| DE | 10251669 B3 | 6/2004 |
| DE | 10328869 A1 | 1/2005 |
| EP | 0657215 A1 | 6/1995 |
| EP | 0853238 B1 | 7/1998 |
| EP | 1382394 A1 | 1/2004 |
| JP | 2004264301 A | 9/2004 |
| JP | 2005514633 A | 5/2005 |
| WO | 9204978 A1 | 4/1992 |
| WO | 03059519 A1 | 7/2003 |
| WO | 2004040975 A2 | 5/2004 |
| WO | 2004042341 A2 | 5/2004 |
| WO | 2005007290 A1 | 1/2005 |

* cited by examiner

SAMPLE SUPPORT AND SAMPLE STORE, ESPECIALLY FOR THE CRYOPRESERVATION OF BIOLOGICAL SAMPLES

BACKGROUND OF THE INVENTION

The invention relates to a sample carrier for at least one biological sample, especially for the cryopreservation of the biological sample, to a sample storage with a plurality of sample carriers designed to receive at least one biological sample, and to a method for the cryopreservation of biological samples.

The putting of biological samples in a cooled, especially frozen state (cryopreservation) for storage (accumulation) and/or for processing is generally known. Numerous types of sample carriers are known from the practice with different forms, sizes and functions that are selected depending on the concrete requirements of a preservation task. For example, for large sample amounts such as blood or tissue, sample carriers in the form of bags, beakers or cuvettes (so-called cryotubes) are used, whereas for small sample amounts such as cell suspensions, substrates with compartments for the receiving of samples are preferred.

Modular sample carriers are known for the reliable handling of a plurality of individual samples. The modular sample carriers described in DE 102 03 940 A1 are distinguished by the detachable fastening of several substrate parts with compartments for the receiving of samples on a common base part. Advantages for the handling of the samples result from the modular technique, especially in the removal of partial samples or the combination of different sample groups. However, the modular construction of substrate- and base parts can have disadvantages since samples can be exposed in the compartments to environmental influences. In particular, undesired foreign substances from a gaseous or liquid environment or from adjacent compartments can be deposited in the partial samples. Contaminations can reduce the quality of cryosamples or completely destroy the cryosamples. In order to avoid contaminations, DE 102 03 940 suggests the use of a protective foil that, however, represents undesired additional expense for many applications and whose protective action can be limited, especially during the transport of substrate parts, e.g. by mechanical influences.

The objective of the invention is to provide an improved sample carrier to avoid the disadvantages of the conventional techniques, in particular during the depositing of biological samples for the cryopreservation and that is suitable in particular for forming a modular interconnection system for receiving a plurality of samples, and that offers an improved protection of the samples against environmental influences, especially against contaminations from a liquid or gaseous environment or from adjacent sample carriers. Furthermore, the sample carrier shall have a simplified construction and have an improved handling in the construction of the interconnection system consisting of several sample carriers. The objective of the invention also consists in providing an improved sample storage for the separate receiving of a plurality of biological samples with which the disadvantages of the conventional modular sample storages are avoided and that is distinguished by an improved handling, in particular an improved removal of partial samples, an expanded range of application and a low space requirement. The objective of the invention also is to provide an improved method for the cryopreservation to avoid the disadvantages of the conventional techniques.

These objects are solved by a sample carrier, a sample storage and a method of the invention.

SUMMARY OF THE INVENTION

According to a first aspect of the invention the objective of the invention is solved by a sample carrier, in particular for the cryopreservation of biological samples, with a casing part forming a sample receiving space, which casing part is provided with a holding device for fixing at least one sample and with carrier connection elements that are active on opposite sides of the casing part for coupling further sample carriers. The casing part has a wall surrounding the sample receiving space between the casing part ends. The carrier connection elements are formed in such a manner that they fit each other so that they form a connection, closed on all sides, of the casing parts bordering each other in the assembled state of the casing parts of two sample carriers. The carrier connection elements are preferably complementary, formed so that they supplement each other in order to produce the closed connection. The sample receiving space of a sample carrier in accordance with the invention is provided for receiving at least one sample arranged on the holding device of the sample carrier concerned or of an adjacent sample carrier.

The alignment of the carrier connection elements on the casing part defines a reference direction that is also designated here, independently of the concrete connection type and the alignment in space, as stack direction or axial direction of the sample carriers.

According to a further aspect of the invention the objective of the invention is solved by the general technical teaching of providing a sample storage that is composed of at least two sample carriers in accordance with the invention. The sample storage is produced in a modular way from the sample carriers. Advantageously, several functions are fulfilled by one single process in the establishing of the connection of the sample carriers. In the first place, each added sample carrier is firmly positioned. Furthermore, the modular construction of the sample storage is expanded. Moreover, the samples arranged in the receiving spaces are shielded against the outside. Independently of the concrete connection type and the alignment in space, the interconnection system consisting of sample carriers is designated here as a stack.

Advantageously, a modular depositing of samples in closed receiving spaces is made possible with the sample carrier in accordance with the invention, so that a contamination of samples from the environment is excluded. Since each sample carrier is provided with a holding device for fixing at least one sample, the samples are localized separated from each other in the sample storage so that even a mutual contamination of samples is prevented. Additional measures for the covering of samples such as a protective foil can be dispensed with. The construction of the sample carrier and of the sample storage as well as the handling of the samples are considerably simplified.

According to a preferred embodiment of the invention (first embodiment) the holding device of the sample carrier is a bottom element that extends over the cross-sectional surface of the casing part, preferably on one of the casing part ends. The sample receiving space in the casing part is advantageously closed on one side with the bottom element, preferably in the form of a plane wall or plate. If several bottom supports are connected via the carrier connection elements, a stack of sample carriers is formed in the assembled state whose sample receiving spaces are separated from each other by one bottom element each. The first embodiment of the sample carrier in accordance with the invention therefore has the special advantage that a contamination between different samples is excluded, not only by their spatial separation but additionally by providing a wall, each formed by the bottom element between the two bordering sample spaces. Sample carriers with samples of a different origin can be assembled without the danger of a mutual influencing being present.

In the first embodiment of the sample carrier in accordance with the invention the casing part forms, together with the bottom element, a cup form on whose first, open end a first carrier connection element is provided and on whose second end, closed by the bottom element, a second carrier connection element is provided on the outside of the bottom element. The form of both carrier connection elements is selected in such a manner that the first and second carrier connection elements of adjacent casing parts cooperate in order to form the closed connection. The receiving spaces in the assembled state of the sample storage are closed on all sides by the provision of the bottom element.

In general, the sample can be directly deposited in the sample receiving space delimited by the wall of the casing part and by the bottom element. However, a preferred variant of the invention provides that the bottom element comprises at least one compartment for receiving the sample. A compartment is a separate container that is connected to the bottom element and whose form and size can be selected as a function of the desired application. The individual sample volumes can advantageously be preset in a defined manner with the compartment. This results in advantages for the depositing as well as for the storage of at least one partial sample in the sample carrier. In particular, conventional depositing techniques, e.g., with pipettes, syringes or other liquid supply devices can be used.

A further important advantage of the invention consists in that there are no limitations as regards the form and size of the at least one compartment that is arranged on the bottom element in the sample receiving space. The compartment can comprise, e.g., a capillary that can be advantageously loaded with the sample under the action of capillary forces. A capillary has the additional advantage that there are no limitations in the space for the orientation of the sample carrier or of the sample storage with a plurality of sample carriers. Alternatively, the compartment can comprise a rather large container such as a flat dish, that has advantages for the cryopreservation of cell cultures, or a beaker, that has advantages for the cryopreservation of large sample volume such as of blood samples.

Several compartments can be provided on a bottom element of a sample carrier. Advantageously, this allows a further fractionation of a sample arranged in the sample carrier into partial samples and/or the provision of reference samples in the sample carrier.

Preferably, the at least one compartment is arranged on the side (inner side) of the bottom element facing the sample receiving space of the associated casing part so that a sample is protected at least mechanically even in the state in which the sample carrier is separated from the sample storage. Alternatively, the at least one compartment can be arranged on the side (outer side) of the bottom element opposite the sample receiving space of the associated casing part. In this instance advantages for the loading of the compartment or the access to the sample can result.

If the bottom element comprises a sealing element on a side opposite the at least one compartment, e.g., on the outer side opposite the sample receiving space, this results in advantages for the sealing of the compartment in the interconnection system of the sample carriers. The at least one compartment in the sample receiving space of each adjacently located sample carrier is tightly closed with the sealing element, e.g., consisting of an elastic material of the one sample carrier. This advantageously leads to a simplification of the handling of the sample storage in such a manner that an exiting of the sample from the compartments is prevented not only in capillary compartments but also in larger compartments such as dishes and/or beakers independently of the orientation of the sample storage.

According to a further variant of the invention the bottom element comprises one single substrate or a stack of several substrates adapted for adherently adhering of at least one sample, e.g., in the form of a liquid layer or of a drop-shaped sample. This instance results in advantages for the loading of the sample carrier with suspension samples.

According to a further preferred embodiment of the invention (second embodiment) the holding device comprises a clamping element connected to the casing part of the sample carrier. The clamping element is arranged in such a manner that a clamping connection can be established to a longitudinally extended sample chamber, e.g., to a hose-shaped or tubular sample chamber that extends through the sample receiving space or extends in the assembled state of the sample storage through a plurality of adjacent receiving spaces. The clamping element fulfills several functions. In the first place, the sample carriers and the sample chambers are fixed relative to each other. In the second place, the longitudinally extended sample chamber consisting of a flexible material, is squeezed together on the clamping element so that in the assembled state of the sample storage partial samples are separated from each other between the clamping elements. Finally, constrictions of the sample chamber are formed on the clamping elements that form predetermined breaking points in the state of cryopreservation, in particular in the frozen state, and thus facilitate a secure removal of partial samples.

According to a preferred variant of the invention the clamping element projects on one of the ends of the casing part. In the assembled state of adjacent sample carriers the clamping element is located in the connection element or in the sample receiving space of the adjacent casing part. The connecting element and/or the sample receiving space is provided with an inner contour that forms a butting face for the clamping element. During the assembling of sample carriers the clamping element is deformed on the butting face and is thus automatically converted into a clamping state.

A further advantage of the sample carrier in accordance with the invention consists in the variability in the selection of a connection type between the carrier connection elements of adjacent sample carriers. Advantages can result for the stability of the sample storage with a bayonet or screw connection. The assembly of the sample carriers is simplified with a plug connection, that is preferred in particular in the second embodiment of the invention and with a magnet connection. The carrier connection elements are preferably designed in such a manner that in the assembled state the receiving spaces of the sample storage are closed in a gas-tight manner to the environment.

A further advantage of the invention consists in the high variability in the selection of the form of the sample receiving space and of the casing part. The casing part can have the form, e.g., of a parallelepiped. This variant can be advantageous for the tight arrangement of sample carriers and sample storages. As an alternative, the form of a straight circular cylinder is provided which results in this instance in advantages for a space-saving, simple assembly of the sample storage and for the compatibility with conventional laboratory apparatuses. According to a preferred variant the casing part is provided with an outside contour forming at least one engagement surface for a tool for applying a torque on the sample carrier. The separation of a sample carrier from a sample storage in the frozen state is facilitated by a torque relative to the stack direction of the sample carriers.

A sample carrier in accordance with the invention can be provided with a cover part detachably connected to one of the carrier connection elements for the one-sided closure of the sample receiving space. A stack of sample carriers in a sample storage can advantageously be closed on one side or on both sides by a sample carrier with a cover part. The cover part advantageously comprises at least one cover connection element formed so that it fits to one of the carrier connection elements of the casing part. Alternatively, a cover connection element can be arranged on each of two opposite sides of the cover part. Each of the cover connection elements is formed so that it fits to one of the carrier connection elements of the casing part. In this instance a cover part can be arranged as intermediate piece in an interconnection system of sample carriers. According to a further variant a cover part can comprise several cover connection elements on one side in order to form a common support for several stacks of sample carriers.

The cover part can advantageously fulfill one or more additional functions in addition to the closure and/or support function(s). To this end the cover part contains in accordance with a further modification of the invention at least one of the following functional devices. Firstly, an electronic circuit such as an electronic memory, a transponder, a computer circuit and/or an RFID system can be provided in order to process information with or on the sample storage to which the cover part is connected, in particular information to be input or output or to be stored. Furthermore, a functional device can comprise an optically detectable marking such as a bar code or a color marking in order to facilitate the identification of a sample storage. According to a further alternative an electrical functional element such as a sensor and/or a display device (e.g., LED) can be provided in order detect or display operating states of the sample storage. Finally, the functional device can be constructed as a mechanical holding element in order to fulfill a support function for the sample storage.

Sample carriers in accordance with the invention can be distinguished according to further modifications in that they contain conduction elements extending in the sample storage in the assembled state of the sample carriers. Conduction elements of one or of several types can be provided. In a first variant conduction elements can comprise electrical conductors for establishing an electrical connection line through the sample carriers and if necessary through the cover parts. Furthermore, optical conductors, e.g., light guide fibers, can be provided that become connected in the assembled state of the sample carriers to a continuous light guide. Furthermore, hollow conductors can be provided for substance transport through which, e.g., a cooling agent such as liquid or vaporous nitrogen can be conducted.

A sample storage in accordance with the invention comprises an interconnection system of a plurality of sample carriers in accordance with the invention of which preferably at least one sample carrier is provided with the cover part. There is advantageously a high variability in the shaping of the interconnection system of sample carriers that can be selected as a function of the concrete requirements of the cryopreservation task. According to a first variant of the invention the sample storage consists of a single row of sample carriers (sample carrier stack). Within the row sample carriers are connected to other sample carriers or cover parts via the carrier connection elements. An advantage of the linear stack of sample carriers consists in the unambiguous association of the individual samples with the sample carrier positions inside the stack.

The stack contains a plurality of separate individual samples in the above mentioned first embodiment of the sample carrier. It is provided in the above-cited second embodiment of the sample carrier that a longitudinally extended sample chamber such as a tubular or hose-shaped sample chamber extends through the linear row of sample carriers and that partial chambers are formed in the individual sample carriers by the compressing of the sample chambers on the clamping elements.

According to a second variant of the invention a 2- or 3-dimensional interconnection system of sample carriers is created (sample carrier packet) by arranging several stacks of sample carriers side by side. In this instance there are advantages from the tight storing of a plurality of sample carriers in the sample carrier packet. The sample carrier stacks can be connected inside a sample carrier packet transversely to the stack direction by storage connection elements, resulting in advantages for the stability of the substrate packet. Alternatively, the sample carrier stacks can be arranged inside a sample carrier packet at a distance from each other. This design results in advantages for the uniform and rapid cooling by a cooling agent that penetrates readily into the sample carrier packet.

According to a further aspect the above mentioned objective of the invention is solved by the general technical teaching of providing a method for the cryopreservation of biological samples in which the samples are deposited in sample carriers in accordance with the invention, the sample carriers are subsequently assembled to a sample storage and the sample storage is then cooled down to a predetermined cryopreservation temperature. Preferred applications of the method are given in the cryopreservation of suspension samples (suspensions of cells, cell groups, cell components), tissue samples or organ samples.

The modular cryostorage technique according to the invention has the following further advantages. The sample storages are self-carrying constructions that as such require no additional holders. They have a high mechanical stability so that an unintended separation of sample carriers inside or outside of a cooling device such as a cryotank, is avoided and a reliable ability to manipulate them by machine is achieved. Sample storages in accordance with the invention can be freely scaled. A sample storage can comprise at least two sample carriers or a considerably larger number of sample carriers, e.g., 100, 1000 or more depending on the sample sizes and sample amounts. Furthermore, the design of the sample carriers makes possible a place-saving arrangement in the form of stacks or packets in the cooling device.

Further advantages result when accessing individual samples in the interconnection system of sample carriers in a sample storage. Short access times are important in the cryopreservation when removing individual samples from a rather large interconnection system in order to avoid an unintended warming of the samples. A rapid access is facilitated with the sample storages in accordance with the invention since only one connection between adjacent connection elements has to be loosened, independently of the number of samples that are to be removed. The linking of sample carriers, sample carrier stacks or sample carrier packets with functional devices such as markings, electronic chips or other additional elements makes possible a broad functionality when managing the samples, e.g., in a cryobank. The sample storages are suitable for a wireless, wire-connected or optical data transfer even in the cooled state at temperatures of, e.g., down to −200° C. The individual sample carriers can carry a marking such as the color marking, the transponder, a certain electrical resistance, a conduction element or a glass fiber that makes an identification possible by the position of the sample carrier inside the sample storage or fulfills another additional function.

The firm connection of the individual sample carriers (optionally with at least one cover part) to a total system makes the manufacture of electrical or optical lines possible. According to the invention the coherence of the sample storage can be monitored by measuring the permeability, e.g., of the electrical resistance or of the transmission of these lines even in the cooled state.

BRIEF DESCRIPTION OF SEVERAL VIEWS OF THE DRAWINGS

Further details and advantages of the invention become apparent from the description of the attached drawings.

DETAILED DESCRIPTION OF PREFERRED EMBODIMENTS

Figure 1:
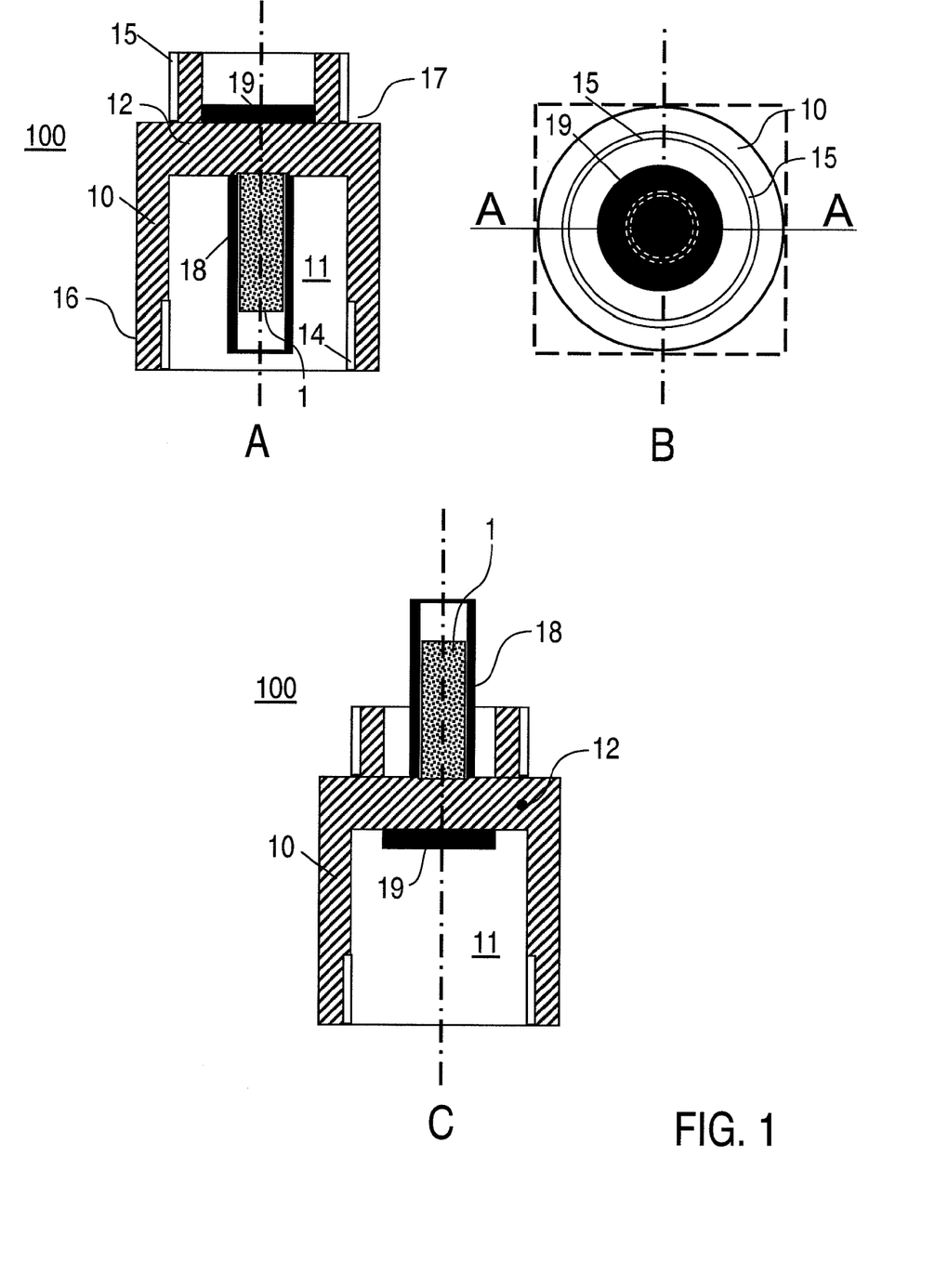
FIG. 1 shows different variants of the first embodiment of the sample carrier in accordance with the invention.

The first embodiment of the sample carrier 100 in accordance with the invention comprises, as is shown in FIG. 1 with different variants, the casing part 10 with the sample receiving space 11. The variants differ in the function of the casing part as receptacle for the sample 1 belonging to the sample carrier (FIGS. 1A, 1B) or as receptacle for a sample belonging to an adjacent sample carrier (FIG. 1C).

The casing part 10 has the form of a hollow cylinder. Carrier connection elements 14, 15 are arranged on the axial casing part ends 16, 17. The carrier connection elements 14, 15 are designed to form a screw connection and comprise therefore an internal threading 14 on the open casing part end 16 and comprise a cylindrical projection 15 with an external threading on the opposite casing part end 17.

Figure 2:
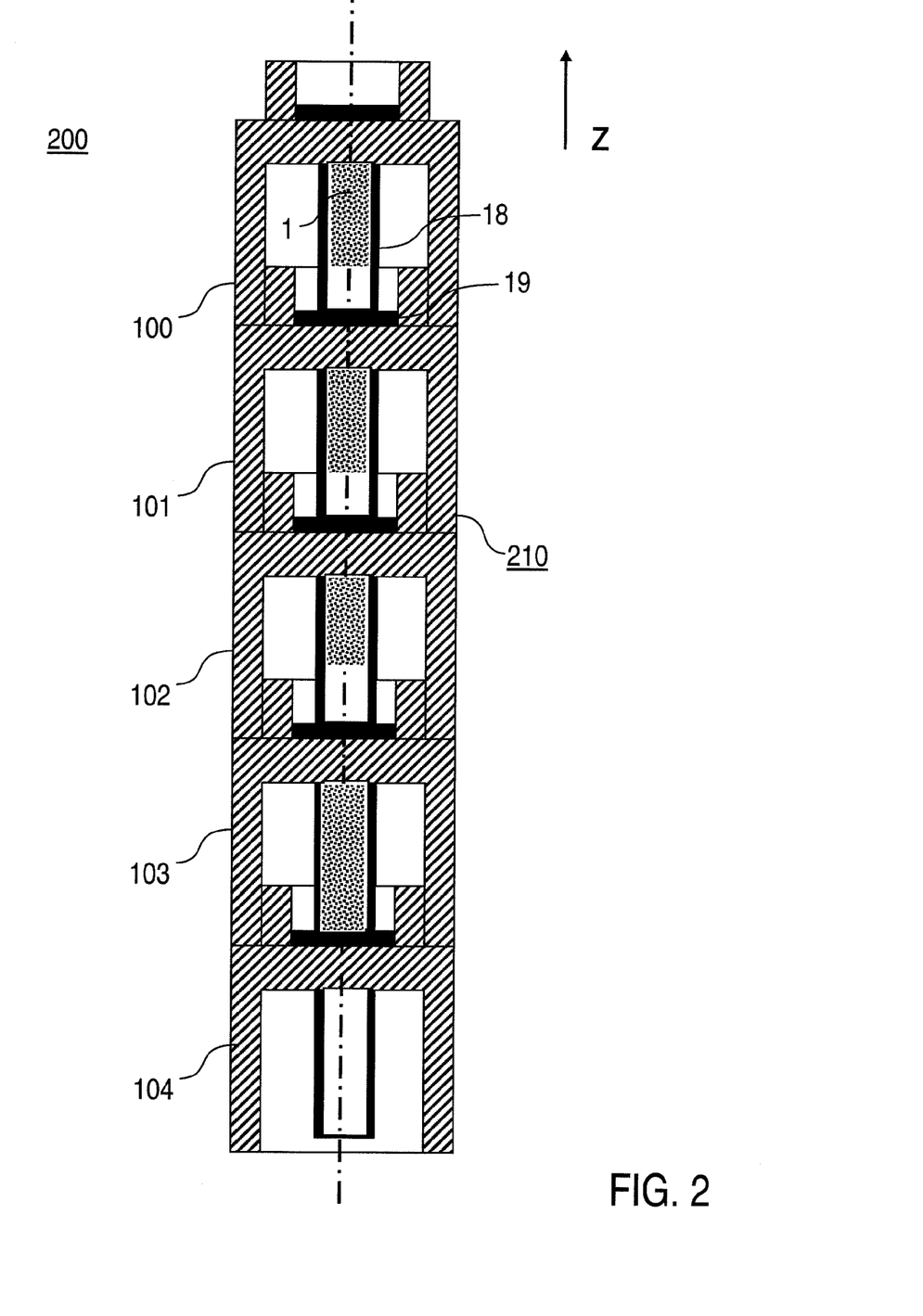
FIG. 2 shows a sample storage with several sample carriers according to FIG. 1A in a schematic sectional view.

The reference direction is given by a connecting line between the casing part ends 16, 17 that runs parallel to the wall of the casing part 10, which reference direction forms the stack direction z for a plurality of assembled sample carriers 100 (see FIG. 2). For the casing part 10 with the illustrated hollow cylindrical form the stack direction and the alignment of the axis of the casing part 10 are identical.

The casing part 10 is manufactured from a plastic material, e.g., polyethylene, polyurethane, PTFE or the like that is also stable at low temperatures, or from a metal, e.g., Al, steel or Cu. The casing part 10 with the bottom element 12 and the carrier connection elements 14, 15 is manufactured, for example, by injection molding. The axial length of the casing part 10 is selected, for example, in the range of 0.1 mm to 100 mm and the diameter is, e.g., 0.5 mm to 30 mm.

According to FIG. 1A the compartment 18 for receiving the sample 1 is located in the sample receiving space 11. In the illustrated example the compartment 18 comprises one single capillary arranged in the sample receiving space 11. In order to fix and align the compartment 18, in the illustrated first exemplary embodiment of the sample carrier 100 the bottom element 12 is provided that extends over the cross-sectional surface of the casing part 10 and forms the closed casing part end 17. The capillary-shaped compartment 18 is fastened at its foot on bottom element 12 at a distance from the circumferential wall of casing part 10. The fastening takes place, for example, by inserting the capillary-shaped compartment 18 into a bore in the bottom element 12. The capillary-shaped compartments 18 can comprise a ventilation opening (not shown) at their foot points.

The cylindrical projection 15 contains a hollow space in which an elastically deformable plastic layer, e.g., of PTFE is arranged on the outside of bottom element 12 as sealing element 19. In general, the length of the compartment 18 projecting into the sample receiving space 11 and the thickness of the sealing element 19 are selected in such a manner that that during the establishing of the connection from the sample carrier 100 to another sample carrier the compartment 18 is closed by sealing element 19. As an alternative to or additionally to the positioning of the sealing element 19 on the outside of bottom element 12 another sealing element can be arranged on the free edge of the compartment 18 (not shown).

The top view in FIG. 1B shows the axially symmetrical construction of the casing part 10 with the upper carrier connection element 15 and the sealing element 19. As a deviation from the hollow cylindrical form of the casing part 10 shown, the latter can have an external form with plane partial surfaces such as a parallelepiped (see dotted line in FIG. 1B) or a prism and a cylindrical internal shape in order to form the sample receiving space 11 and the internal threading 14. If the external form is delimited by plane surfaces then engagement surfaces for a tool for separating, in particular for screwing off a sample carrier or a sample carrier group from the sample storage are advantageously formed. A sufficiently high torque can be exerted on the sample carrier with the tool, such as a monkey wrench, socket wrench or the like, so that the removal of sample carriers is possible without problems even at low temperatures.

In the variant according to FIG. 1C the compartment 18 for receiving the sample 1 is located outside of the sample receiving space 11. In the assembled state of several sample carriers the compartment 18, e.g., the individual capillary, is enclosed in the sample receiving space of the adjacent sample carrier. In a corresponding manner the sealing element 19 is provided on the inside of the bottom element 12 as elastically deformable plastic layer.

FIG. 2 shows a sample storage 200 in accordance with the invention comprising a single stack 210 with several sample carriers 100, 101, 102, . . . in accordance with FIG. 1A. The combination of sample carriers according to FIG. 1C is correspondingly possible. The sample carriers 100, 101, 102, ... are arranged immediately adjacent to each other in stack 210 in stack direction z by the connection between the carrier connection elements (internal threading 14 on the open casing part end 16 and cylindrical projection 15 with external threading on the closed casing part end 17, see FIG. 1A). The compartment 18 in one of the sample carriers 100 is closed with sealing element 19 of the adjacent sample carrier. A gas-tight closure of the sample receiving spaces in the interconnection system of the sample storage 200 is already achieved by the screwed carrier connection elements. In order to improve the tightness, support seals can additionally be provided (see FIG. 7).

The compartment 18 consists of a biocompatible and cryostable material, such as glass or plastic. The forms and sizes of the sample carriers 100, 101, 102, ... and of the compartments 18 are selected as a function of the concrete preservation task. Accordingly, the dimensions and proportions of these structural parts can vary greatly. The holding capacity of a compartment can be, e.g., up to 1:1 or above.

The cryopreservation of a sample 1 with the sample storage 200 takes place in such a manner that at first the sample 1 divided into partial samples or in combination with a reference sample is deposited in several sample carriers 100, 101, 102, .... This takes place with the capillary-shaped compartments 18 via a sucking up under the action of capillary forces. According to the invention a control substance can be arranged in one of the sample carriers. The control substance is distinguished, e.g., by an interaction with the sample 1 when they come in contact with one another. For example, a toxic substance can be used as control substance that results in the destruction of the sample upon the occurrence of a leakiness of the sealing element 19 or of the wall of the compartment 18. Furthermore, sample 1 and control substance 1 can form a two-component system that does not react until mutual contact. The providing of a control substance makes possible an internal quality control in each of the sample carriers.

Figure 6:
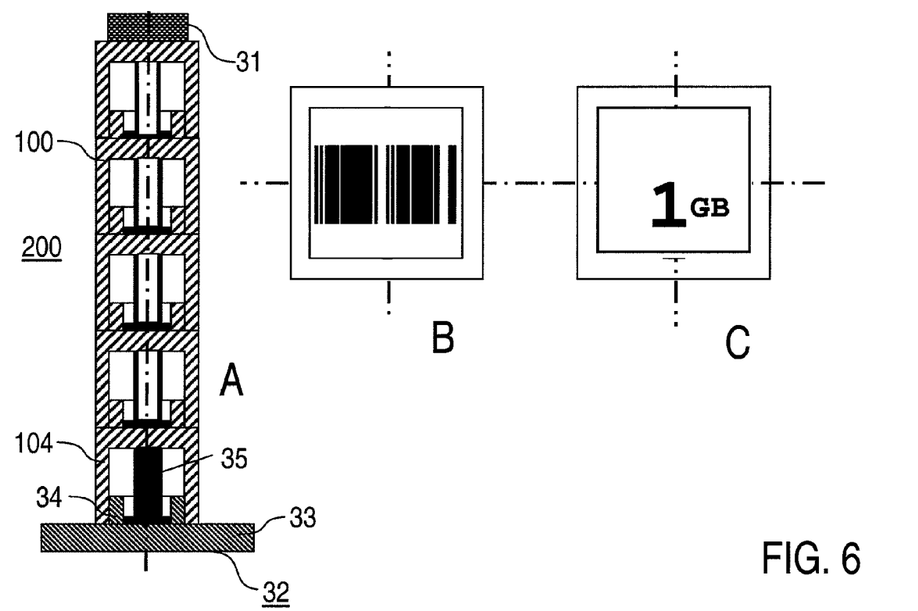
FIGS. 6 to 10 show different variants of sample storages in accordance with the invention in a schematic sectional view.

The connection of the sample carriers 100, 101, 102, ... subsequently takes place in order to form the linear stack 210. A sample carrier 104 without a sample or alternatively a cover part (see, e.g., FIG. 6) is attached on the open end of the stack 210 as shown. The loaded sample storage 200 is subsequently transferred into an environment of reduced temperature, e.g., a cooling device such as a cryotank with a temperature in the range of −30° C. to −200° C.

Figure 3:
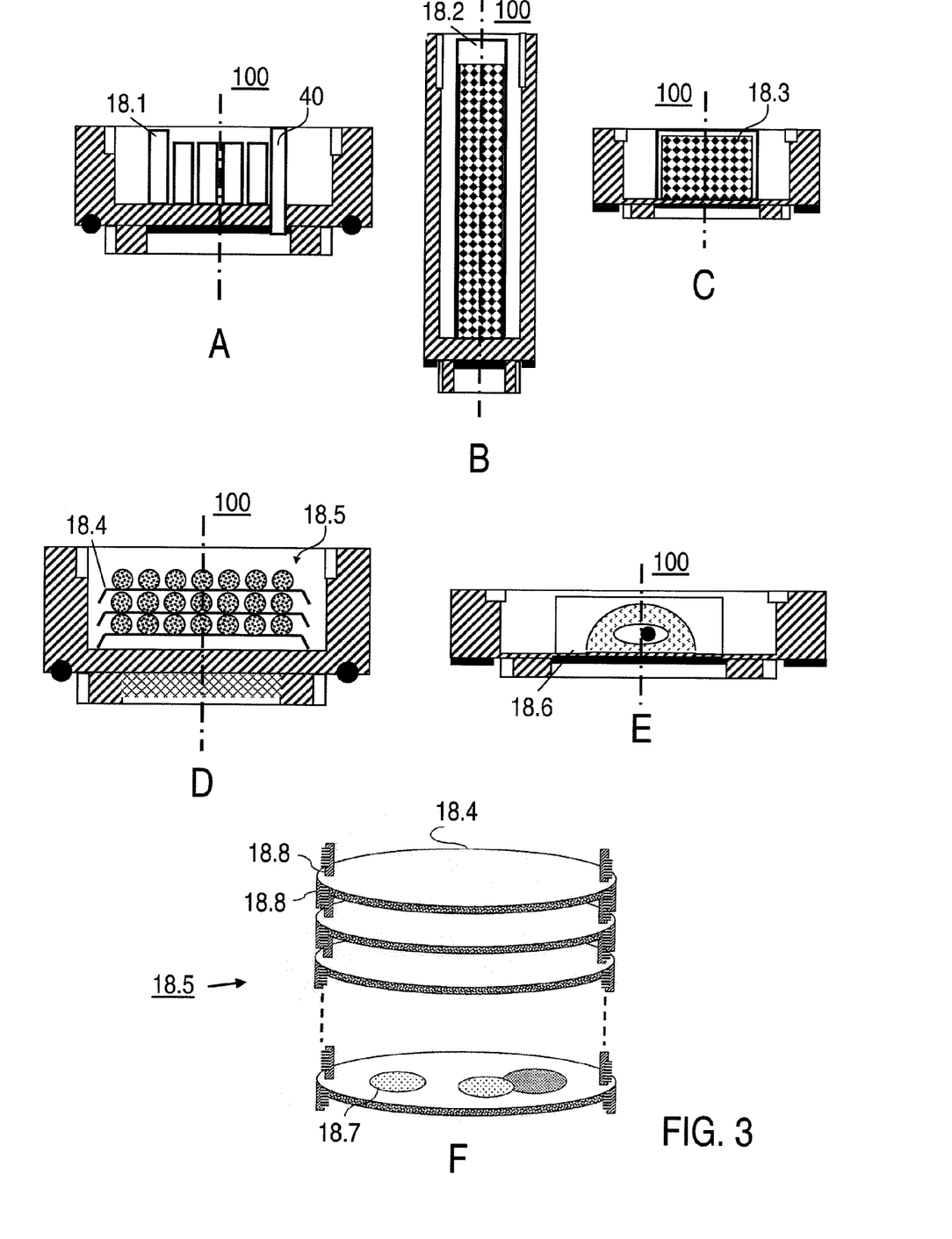
FIG. 3 shows further variants of the first embodiment of the sample carrier in accordance with the invention in a schematic sectional view.

FIG. 3 shows different variants of the first embodiment of the sample carrier 10 in accordance with the invention in which an array of capillary-shaped compartments 18.1 (FIG. 3A), a beaker compartment 18.2 (FIG. 3B), a dish compartment 18.3 (FIG. 3C), a substrate stack 18.5 (FIG. 3D) with several substrates 18.4 for the adherent adhering of drop-shaped samples (FIGS. 3D and F) or an individual drop receptacle 18.6 (FIG. 3E) are arranged. The features of FIGS. 3A to 3F can be provided in accordance with a sample carrier according to FIG. 1C.

The capillary array according to FIG. 3A has the advantage that the individual capillaries 18.1 can be separately filled and individually inserted into bottom element 19. In a corresponding manner, individual partial samples can be removed, e.g., broken off from the sample carrier 100 even in the frozen state.

FIG. 3A illustrates by way of example the provision of a conduction element 40 on the sample carrier 100. The conduction element comprises at least one optical fiber 40 extending through the casing part 10 and the bottom element 12 with the seal 19. In the assembled state of several sample carriers 100 the optical fibers are combined to a continuous optical conductor. In an analogous manner one or several electrical conductors or hollow conductors can be provided for substance transport. In a corresponding manner at least one conduction element 40 can be integrated into a sample carrier in accordance with the other variants or with the second embodiment of the invention.

The variants according to FIGS. 3D and 3E are especially well suited for the receiving of suspension drops. The drops are deposited on the substrates 18.4 or in the individual drop receiver 18.6 and held in a stationary manner in the adherent state even during the joining together of a plurality of sample carriers 100 to a sample storage and during the following cooling off. The individual drop receiver 18.6 is designed to receive individual cells or small cell groups such as animal or human stem cells, differentiated cells or egg cells and has a diameter of e.g., 1 mm to 5 mm.

FIG. 3F illustrates further details of the substrate stack 18.5. Disk-shaped substrates 18.4, that consist, e.g., of plastic, aluminum or textile fabric and optionally have structured areas 18.7 on the substrate surface for the adherent adhesion of cells, are connected above each other via screw elements 18.8 in the shape of a stack. The diameter of the substrates is selected in the range of 1 mm to 30 cm.

FIGS. 3A to 3E show carrier seals 17.1 that can be provided circumferentially on one of the casing part ends 17 and improve the gas-tight closure of the sample receiving space and the interconnection system of the sample storage.

Figure 4:
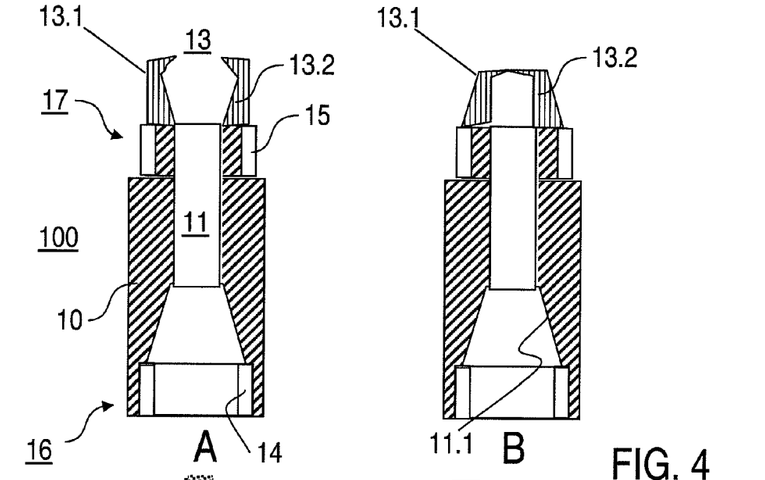
FIG. 4 shows the second embodiment of the sample carrier in accordance with the invention in a schematic sectional view.
Figure 5:
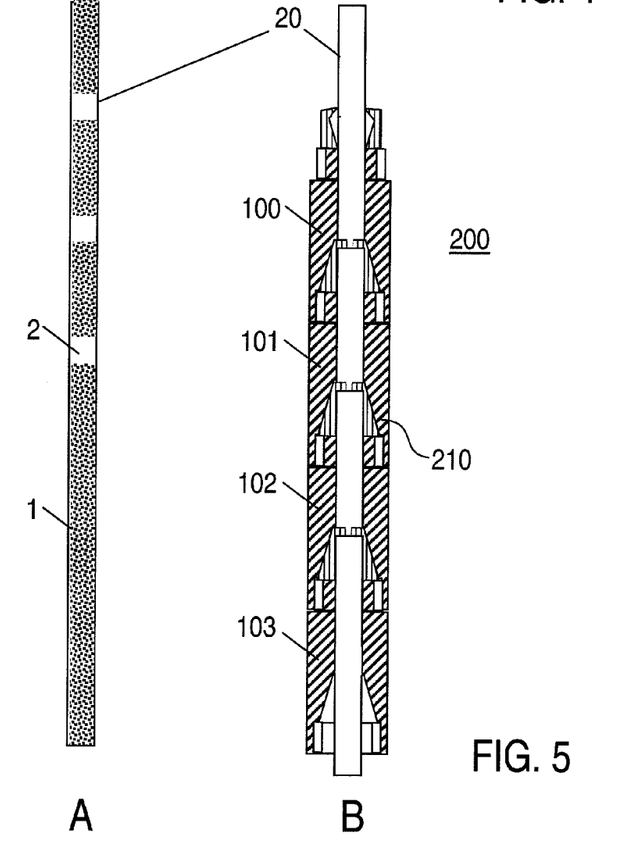
FIG. 5 shows a sample storage with a plurality of sample carriers according to FIG. 4 in a schematic sectional view.

The FIGS. 4 and 5 show the second embodiment of the sample carrier 100 in accordance with the invention with the casing part 10, the inner sample receiving space 11 and the holding device 13. Carrier connection elements 14, 15 are provided on the axial casing part ends 16, 17 and form, e.g., a screw connection as described above.

In distinction to the first embodiment of the sample carrier 100 the holding device does not comprise a continuous bottom element but rather the clamping element 13. The clamping element 13 comprises two clamping arms 13.1, 13.2 flexibly attached to the upper casing part end 17 or to the corresponding carrier connection element 15. In the relaxed state (FIG. 4A) of the clamping element 13 the clamping arms 13.1, 13.2 run in axial direction so that a distance is formed between the ends of the clamping arms 13.1, 13.2. In a clamping state in accordance with FIG. 4B the ends of the clamping arms 13.1, 13.2 are bent radially inward so that a part of a sample chamber located in this area is squeezed together. The inner contour of the sample receiving space 11 is provided with a butting face 11.1 that fits the clamping element 13 so that in the connection of two sample carriers the clamping arms 13.1, 13.2 are bent together. Advantageously, the clamping state is therefore forcibly adjusted with a sample carrier 100 being connected to an adjacent sample carrier.

The practical application of the second embodiment of the sample carrier 100 is schematically illustrated in FIG. 5. In FIG. 5A a hose-shaped sample chamber 20 is shown with a suspension sample 1. The sample chamber is filled with the suspension sample 1 continuously or with partial samples that are separated from each other by gas bubbles 2 (see DE 102 51 721). The sample chamber 20 can comprise constrictions with distances corresponding to the distances of the clamping elements 13 in the assembled sample storage with the constrictions facilitating the pressing together of the sample chamber 20 in the sample storage.

In FIG. 5A the sample storage 200 is shown with a linear stack 210 of sample carriers 100, 101, 102, ... in accordance with the invention and in accordance with the second embodiment. The sample chamber 20 extends through the entire stack 210 of the sample storage 200. In the assembled state of the sample carriers 100, 101, 102, . . . the clamping element 13 is in the clamping state so that the sample chamber 20 is squeezed together at regular distances and is subdivided into partial samples.

The sample storage according to FIG. 5 is assembled in that at first the sample carriers 100, 101, 102, . . . are pushed onto the sample chamber 20 and subsequently connected to each other during which at each connection the associated clamping element 13 is transferred into the clamping state. In an advantageous manner, no mechanical damage is caused in the sample, e.g., to biological cells, since the transfer into the clamping state takes place in the warm state, during which the sample is still liquid so that sample components can escape during clamping into other areas of the sample chamber 20.

Cutting tools can be arranged on the ends of the clamping arms 13.1, 13.2 which divide the sample chamber 20 into individual chambers already during the assembly of the sample storage 200. In this instance the tightness and mutual separation of the partial samples in the partial chambers are ensured by the ends of the clamping arms 13.1, 13.2 resting flush against one another in the clamping state. Alternatively, it can be provided that the walls of the sample chamber 20 can first be pressed together with the cutting tools without being cut through and a cutting through of the sample chamber 20 is facilitated only in the cooled state during the removal of sample carriers or of sample carrier groups.

The FIGS. 6 to 10 illustrate by way of example the combination in accordance with the invention of sample carriers or sample storages with one or several similar or different cover parts. In general, a cover part comprises an additional structural part that can be connected to one of the casing part ends in order to form a closure or an intermediate piece in a stack of sample carriers. To this end the cover part comprises at least one cover connection element that is complementary to the particular carrier connection elements of the sample carriers. Since the cover parts can fulfill different functions and are provided to this end with certain function devices, the cover parts can have different structural forms depending on the position in the sample storage and on the function.

FIG. 6A shows two types of cover parts 31, 32. The first cover part 31 has a cup form with an internal threading that fits the carrier connection element of the uppermost sample carrier 100. The cover part 31 forms a closure of the uppermost sample carrier 100. In addition, an electronic chip, a transponder or an RFID system or a marking such as a linear or multi-dimensional barcode can be integrated into cover part 31.

A base part 32 with a radially extending platform 33 is shown on the lower end of sample storage 200. A base part 32 is screwed into the lowest sample carrier 104 with the cover connection element 34. Furthermore, the base part 32 is provided with the sensor 35 that serves, e.g., to measure temperature, vibrations, acceleration or torques. Further electronic components such as multiplexers, amplifiers and the like can be integrated into the base part 32 that are adapted to the operating temperatures during the cryopreservation. Furthermore, the platform 33 can comprise a marking, e.g., a barcode or a memory chip, as is schematically shown in FIGS. 6B and 6C.

A further function device that can be integrated into the cover part 32 comprises a monitoring element that indicates a heating by a structural change (e.g., melting of a frozen ice ball) or by a color change. Furthermore, the cover part can have a cooling capacity for removing heat from the sample carriers for the duration of manipulations on the cooled sample storage outside of a cooling device.

Figure 7:
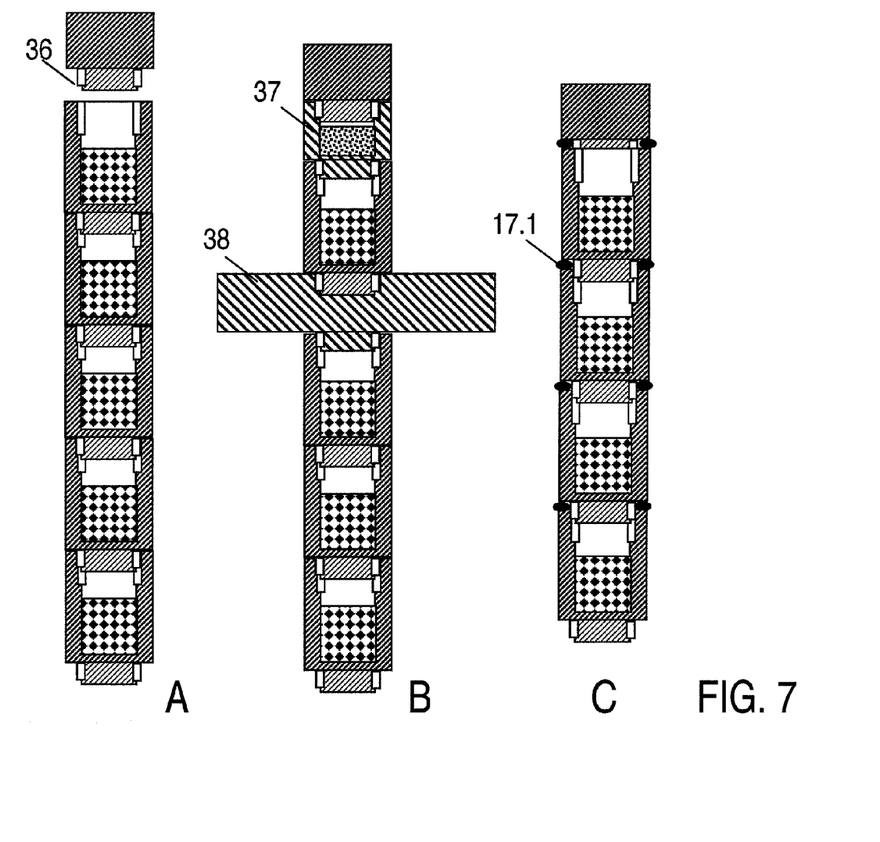

FIG. 7 shows further examples of cover parts used in accordance with the invention that are formed as closure plug 36 (FIG. 7A) or intermediate piece 38 (FIG. 7B). The closure plug 36 can be provided with an additional seal 37 (FIG. 7B) that serves for a complete closure of the sample storage and consists, e.g., of PTFE or a similar temperature-stable material. The additional seal 37 is preferably used in the cryopreservation of samples in liquid nitrogen or in the cryopreservation of pathogenic samples. FIG. 7C shows the action of the carrier seals 17.1. illustrated in the FIGS. 3A to 3E.

Instead of the additional seal 37 a further reservoir can be provided in which a reference solution or a marker substance is arranged for indicating an inadmissible temperature change. The marker substance can display a color change or form change (e.g., melting of balls) when certain temperature limits are exceeded.

Figure 8:
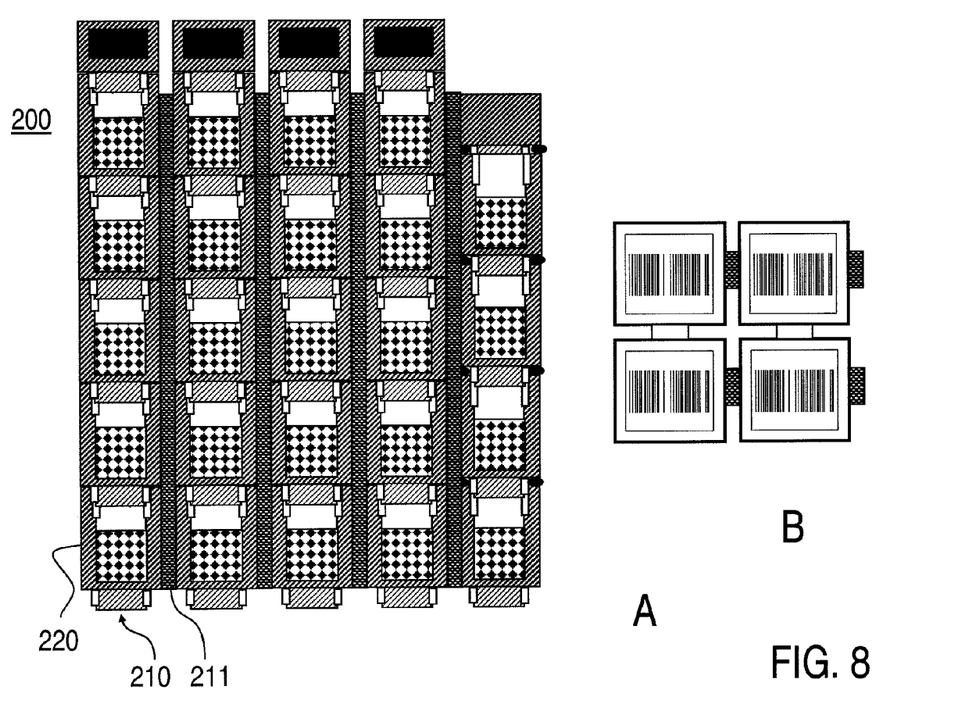

FIG. 8 illustrates the formation of a sample storage 200 with a 2- or 3-dimensional sample carrier packet 220. Individuals sample carrier stacks 210 are connected to each other via lateral stack connection elements 211 comprising, e.g., rails, clip connections or plug-in connections.

Figure 9:
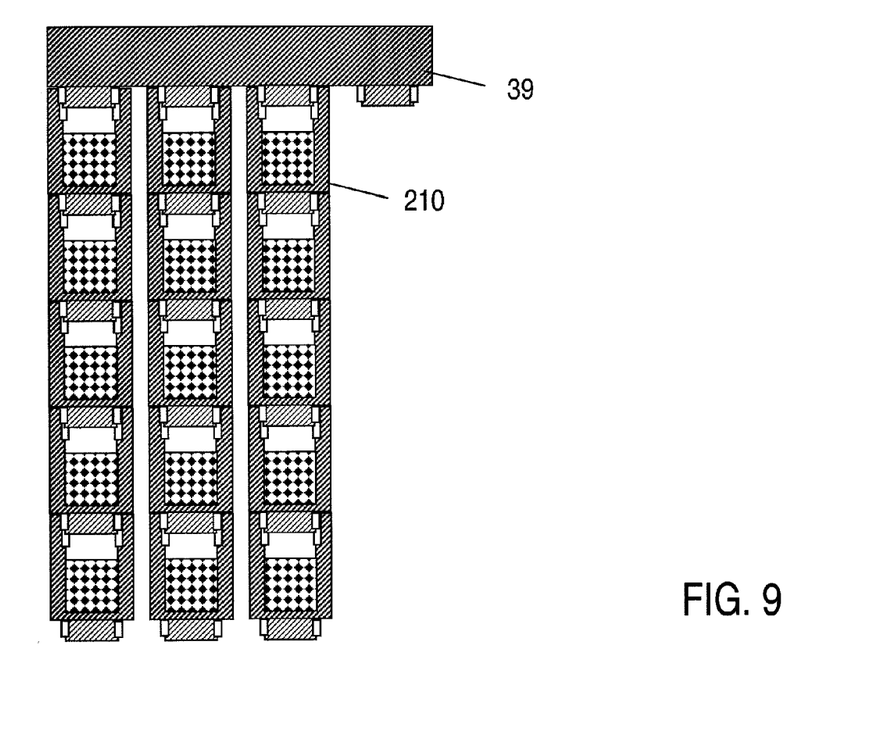
Figure 10:
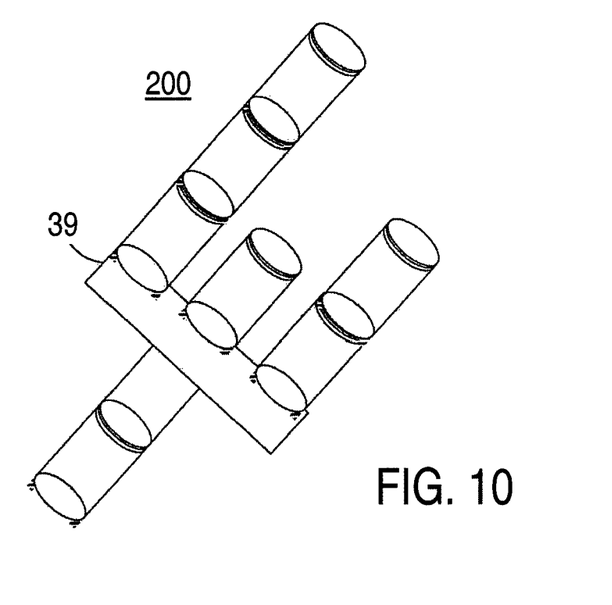

Alternatively, a sample storage 200 can be formed with a sample carrier packet via common cover part 39 for a plurality of sample carrier stacks 210 (FIGS. 9, 10). This variant has the advantage that the sample carrier stacks 210 are arranged at distances from each other and can thus be more readily loaded with a cooling agent. The variant of a common cover part for a plurality of sample carrier stacks can be modified according to FIG. 10 in such a manner that a self-carrying total system of sample carriers 10 is created with the geometric form and the arrangement of the individual sample carriers illustrating the biological sample hierarchy, e.g., cell generations or cell passages.

The features of the invention disclosed in the previous description, the drawings and the claims can be significant individually or also in combination for the realization of the invention in its different embodiments.

The invention claimed is:

1. A sample carrier for cryopreservation of a biological sample, comprising:
 a casing part defining a sample receiving and having two casing part ends at opposite ends of the casing part,
 a holding device on which the sample can be arranged, wherein the holding device includes a bottom element with which the sample receiving space is closed on one end of the casing part such that the bottom element of the holding device is formed by said closed end of the casing part;
 carrier connection elements that are arranged on the casing part ends and that are directed to opposite casing part ends and are formed in such a manner that said carrier connection elements fit one another so that at least two casing parts can be assembled, said carrier connection elements forming a connection between said at least two assembled casing parts, said connection being closed on all sides in a gas-tight manner;
 at least one separate sample container having a shape of a capillary, tube or beaker and being fixed on the bottom element at a first end thereof, the at least one separate sample container configured to receive the sample in a liquid state and to contain the sample disposed therein; and a seal consisting of a substantially flat sealing element including an elastically deformable plastic layer arranged on a second side of the bottom element opposite the first side of the bottom element that is fixed to the at least one separate container, the plastic layer being configured to tightly close a separate sample container having a shape of a capillary, tube or beaker and being arranged within a sample receiving space of an adjacent sample carrier.

2. The sample carrier according to claim 1, wherein a plurality of containers for receiving the sample is arranged on the bottom element.

3. The sample carrier according to claim 1, wherein the bottom element comprises at least one substrate for adherent adhering of at least one sample.

4. The sample carrier according to claim 3, wherein the bottom element comprises a substrate stack for the adherent adhering of a plurality of samples.

5. The sample carrier according to claim 1, wherein the at least one container is arranged on a side of the bottom element facing the sample receiving space of an associated casing part.

6. The sample carrier according to claim 1, wherein the at least one container is arranged on a side of the bottom element opposite the sample receiving space of an associated casing part.

7. The sample carrier according to claim 1, wherein the carrier connection elements are set up to produce at least one connection type selected from the group consisting of a bayonet connection, a screw connection, a plug-in connection and a magnet connection.

8. The sample carrier according to claim 1, wherein the sample receiving space can be closed gas-tight on each of the casing part ends with placed-on casing parts of further sample carriers.

9. The sample carrier according to claim 1, wherein the casing part has an outer contour that forms at least one engagement surface for a tool.

10. The sample carrier according to claim 1, wherein the casing part carries a cover part on one of the casing part ends.

11. The sample carrier according to claim 10, wherein the cover part comprises at least one cover connection element formed to fit one of the carrier connection elements of the casing part.

12. The sample carrier according to claim 10, wherein the cover part comprises at least one function device selected from the group consisting of an electronic memory, a transponder, a computer circuit, an RFID system, a marking, a sensor, and a mechanical holding element.

13. The sample carrier according to claim 1, further comprising at least one conduction element extending between the casing part ends.

14. The sample carrier according to claim 13, wherein the at least one conduction element comprises at least one of an electrical conductor, an optical conductor and a hollow conductor for substance transport.

15. A sample storage for cryopreservation of a plurality of biological samples, said sample storage comprising an interconnection system of a plurality of the sample carrier according to claim 1.

16. The sample storage according to claim 15, wherein the interconnection system comprises a stack of sample carriers that are assembled immediately adjacent to each other with the carrier connection elements.

17. The sample storage according to claim 16, wherein the sample connected to one of the sample carriers is arranged in the sample receiving space of the casing part of said sample carrier.

18. The sample storage according to claim 16, wherein the sample connected to one of the sample carriers is arranged in the sample receiving space of the casing part of an adjacent sample carrier.

19. The sample storage according to claim 15, wherein the interconnection system comprises a stack of sample carriers and cover parts that are assembled immediately adjacent to each other with the carrier- and cover connection elements.

20. The sample storage according to claim 15, wherein the interconnection system comprises several stacks of sample carriers arranged adjacent to each other.

21. The sample storage according to claim 20, wherein the stacks of sample carriers are connected radially immediately adjacent to each other by storage connection elements.

22. The sample storage according to claim 21, wherein the stacks of sample carriers are connected radially distanced by a common cover part.

23. A method for the cryopreservation of biological samples in the sample carrier according to claim 1, said method comprising the following steps:
 depositing of samples in the sample carriers,
 connecting of the sample carriers to a sample storage comprising a plurality of the sample carriers, and
 transferring the sample storage into an environment of reduced temperature.

24. The method according to claim 23, wherein the depositing of samples comprises a receiving of the samples in the at least one container of the sample carrier under action of capillary forces.

25. The method according to claim 23, wherein the depositing of samples comprises a receiving of the samples in a hose-shaped sample chamber and wherein a series of casing parts can be drawn onto the sample chamber and connected to each other in order to connect the sample carriers.

26. The method according to claim 23, wherein the samples comprise suspension samples, tissue samples or organ samples.

27. The sample carrier according to claim 1, the bottom element defining a bore, the at least one separate sample container being inserted into the bore.

28. The sample carrier according to claim 1, wherein the at least one separate container is fluid impermeable to isolate the sample disposed within the at least one separate container.

29. The sample carrier according to claim 1, at least one separate sample container being fixed on the bottom element at a first end thereof is below the bottom element, and the casing part extends both above and below the bottom element.

30. The sample carrier according to claim 1, the elastically deformable plastic layer configured to extend across the separate sample container arranged in the sample receiving space of the adjacent sample carrier to close the separate sample container.

* * * * *